US010307297B2

(12) United States Patent
Scheremet et al.

(10) Patent No.: US 10,307,297 B2
(45) Date of Patent: Jun. 4, 2019

(54) PERIPHERAL HYDROGEL WOUND DRESSING

(71) Applicant: FastTrack Medical Solutions LLC, Eden Prairie, MN (US)

(72) Inventors: William Scheremet, Hinckley, MN (US); Steven J. Brinkman, Eden Prairie, MN (US); Kim Jacobsen, Minneapolis, MN (US)

(73) Assignee: FastTrack Medical Solutions LLC, Eden Prairie, MN (US)

( * ) Notice: Subject to any disclaimer, the term of this patent is extended or adjusted under 35 U.S.C. 154(b) by 564 days.

(21) Appl. No.: 14/678,772

(22) Filed: Apr. 3, 2015

(65) Prior Publication Data

US 2015/0209188 A1 Jul. 30, 2015

Related U.S. Application Data

(63) Continuation-in-part of application No. 14/137,757, filed on Dec. 20, 2013, now Pat. No. 9,295,766.
(Continued)

(51) Int. Cl.
*A61F 13/00* (2006.01)
*A61F 13/02* (2006.01)
(Continued)

(52) U.S. Cl.
CPC .......... *A61F 13/0253* (2013.01); *A61F 17/00* (2013.01); *A61L 15/44* (2013.01);
(Continued)

(58) Field of Classification Search
CPC .............. A61F 13/0246; A61F 13/0269; A61F 13/025; A61F 2013/0028; A61F 13/0253;
(Continued)

(56) References Cited

U.S. PATENT DOCUMENTS 2,946,435 A * 7/1960 Schladermundt ... A61F 13/0203
206/441
4,909,244 A 3/1990 Quarfoot et al.
(Continued)

FOREIGN PATENT DOCUMENTS

EP 0630216 B1 9/1999

*Primary Examiner* — Kim M Lewis
(74) *Attorney, Agent, or Firm* — Craige Thompson; Thompson Patent Law

(57) ABSTRACT

Apparatus and associated methods for a hydrogel wound covering membrane may include a backing layer and a release liner each having high pliability for permitting the membrane to be folded without pinching a sandwiched hydrogel layer thereby preventing its thinning in folded regions. In an illustrative embodiment, the hydrogel layer may annularly circumscribe a central wound region of the membrane. The thickness of the annulus may be selected to prevent water from penetrating the annulus for water exposures of a predetermined length of time. In some embodiments, a gauze may be affixed to a central portion of the membrane for gentle contact with a wound when the membrane is affixed to a wounded person. The membrane may advantageously maintain a substantially uniform hydrogel thickness when folded or rolled, so as to permit secure annular adhesion circumscribing a wound when unfolded or unrolled and applied.

9 Claims, 11 Drawing Sheets

Related U.S. Application Data which is a continuation of application No. 13/647,369, filed on Oct. 8, 2012, now Pat. No. 8,637,725, which is a continuation-in-part of application No. 12/857,522, filed on Aug. 16, 2010, now Pat. No. 8,309,786.

(60) Provisional application No. 61/978,722, filed on Apr. 11, 2014, provisional application No. 61/544,362, filed on Oct. 7, 2011.

(51) Int. Cl.
*A61L 15/58* (2006.01)
*A61L 15/44* (2006.01)
*A61F 17/00* (2006.01)
*A61L 15/46* (2006.01)
*A61L 15/60* (2006.01)

(52) U.S. Cl.
CPC .............. *A61L 15/46* (2013.01); *A61L 15/58* (2013.01); *A61L 15/60* (2013.01); *A61F 13/00063* (2013.01); *A61F 2013/00676* (2013.01); *A61L 2300/404* (2013.01)

(58) Field of Classification Search
CPC . A61F 2013/00063; A61F 2013/00676; A61B 2017/086; A61B 17/08908; A61L 15/42; A61L 15/42425; A61L 15/58
See application file for complete search history.

(56) References Cited

U.S. PATENT DOCUMENTS

| | | | |
|---|---|---|---|
| 5,480,377 A * | 1/1996 | Cartmell | A61F 13/0273 |
| | | | 602/42 |
| 5,489,262 A | 2/1996 | Cartmell et al. | |
| 5,762,620 A | 6/1998 | Cartmell et al. | |
| 5,973,221 A | 10/1999 | Collyer et al. | |
| 6,039,940 A * | 3/2000 | Perrault | A61L 15/60 |
| | | | 424/443 |
| 8,586,818 B2 * | 11/2013 | Aali | A61F 13/0203 |
| | | | 128/893 |
| 8,759,602 B2 | 6/2014 | Buckman et al. | |
| 2003/0088202 A1 * | 5/2003 | Gilman | A61F 13/023 |
| | | | 602/46 |
| 2005/0165445 A1 * | 7/2005 | Buckman | A61F 13/00 |
| | | | 606/213 |
| 2008/0033377 A1 * | 2/2008 | Kauth | A61F 13/00987 |
| | | | 604/304 |
| 2009/0287133 A1 | 11/2009 | LaGreca, Sr. | |
| 2014/0107555 A1 | 4/2014 | Patel | |
| 2014/0309574 A1 | 10/2014 | Cotton | |
| 2014/0336557 A1 | 11/2014 | Durdag et al. | |

* cited by examiner

PERIPHERAL HYDROGEL WOUND DRESSING

CROSS-REFERENCE TO RELATED APPLICATIONS

The instant application is related to and claims priority to the following U.S. patent applications, the entirety of each of which is herein incorporated by reference.

| | | |
|---|---|---|
| 61/978,722 | Hydrogel Wound Covering Membrane Having Antimicrobial and Adhesive Properties | Apr. 11, 2014 |
| 14/137,757 | Kit for Low Profile Thoracic Wound Seal with Laterally-Directed Discharge | Dec. 20, 2013 |
| 13/647,369 | Kit for Low Profile Thoracic Wound Seal with Laterally-Directed Discharge | Oct. 8, 2012 |
| 61/544,362 | Hydrogel Wound Covering Membrane Having Antimicrobial and Adhesive Properties | Aug. 7, 2011 |
| 12/857,522 | Low Profile Thoracic Wound Seal with Laterally-Directed Discharge | Aug. 16, 2010 |

TECHNICAL FIELD

The present application relates to wound coverings and more particularly to a pliable wound covering having antimicrobial properties.

SUMMARY

Apparatus and associated methods for a wound covering membrane provide a carrier substrate having antimicrobial and adhesive agents, such that application of the membrane over a wound promotes the release of the antimicrobial agents to prevent infection and stimulate wound healing. Various embodiments may provide for impregnated adhesive agents or adhesive layers such that the membrane may removably attach to the skin of a patient. Various embodiments may also provide for a malleable, pliable, and otherwise bendable membrane structure to permit the membrane to contour to the supporting structure, for example the skin of the patient.

Apparatus and associated methods for a hydrogel wound covering membrane may include a backing layer and a release liner each having high pliability for permitting the membrane to be folded without pinching a sandwiched hydrogel layer thereby preventing its thinning in folded regions. In an illustrative embodiment, the hydrogel layer may annularly circumscribe a central wound region of the membrane. The thickness of the annulus may be selected to prevent water from penetrating the annulus for water exposures of a predetermined length of time. In some embodiments, a gauze may be affixed to a central portion of the membrane for gentle contact with a wound when the membrane is affixed to a wounded person. The membrane may advantageously maintain a substantially uniform hydrogel thickness when folded or rolled, so as to permit secure annular adhesion circumscribing a wound when unfolded or unrolled and applied.

Various embodiments may have one or more advantages. For example, some embodiments may provide wound isolation from contamination from the surrounding environment. Various embodiments may prevent channeling in the unfolded hydrogel. For example, after unfolding a hydrogel wound covering membrane, the hydrogel/adhesive may retain a uniform thickness. When affixed to a skin surface of a patient, a hydrogel seal may prevent fluid communication between an interior volume and an exterior ambient environment. When affixed to a skin surface of a patient, the uniformly thick hydrogel/adhesion layer may contiguously contact a patient's skin providing wound isolation from an exterior environment. In some embodiments, the hydrogel may provide antimicrobial agents for reducing the risk of wound infections. In an exemplary embodiment, a hydrogel/adhesive layer may provide removable attachment to a patient's skin, wherein while attached, the hydrogel/adhesive may provide a temporary barrier to water penetration.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like or similar elements.

DETAILED DESCRIPTION OF ILLUSTRATIVE EMBODIMENTS

Figure 1:
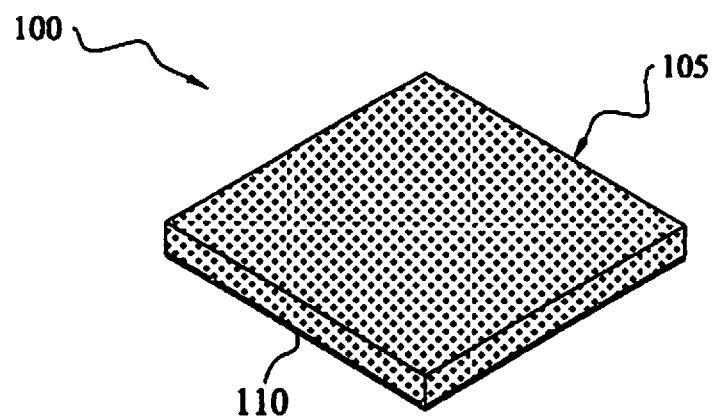
FIG. 1 depicts an upper perspective view of an exemplary membrane.
Figure 2:
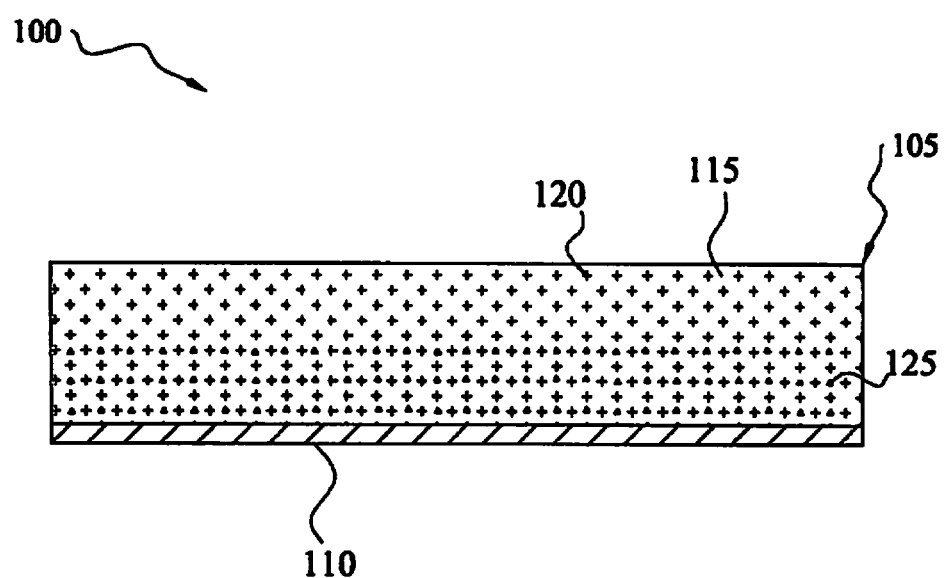
FIG. 2 depicts a cross-sectional view of the embodiment shown in FIG. 1.
Figure 3:
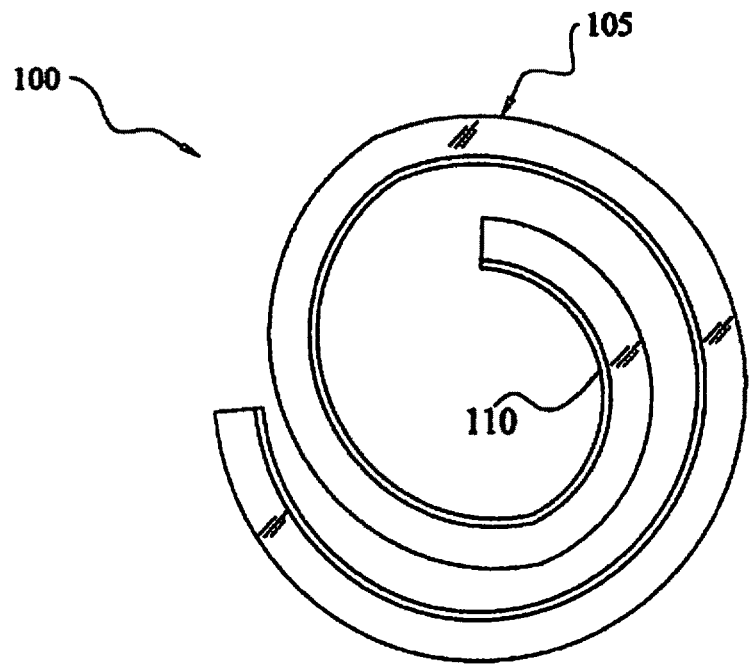
FIG. 3 depicts an exemplary side view of an embodiment illustrating the membrane being rolled.
Figure 4:
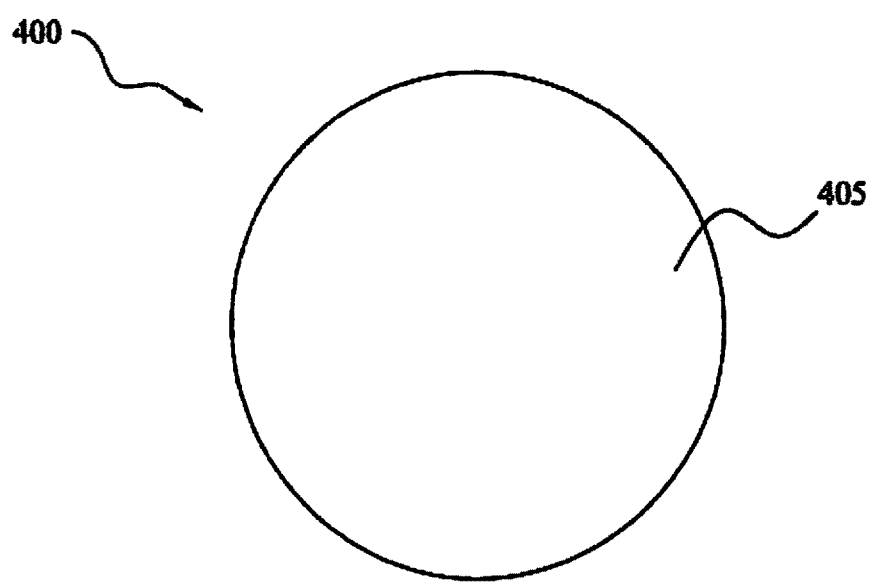
FIGS. 4-6 depict sets of exemplary membranes.
Figure 5:
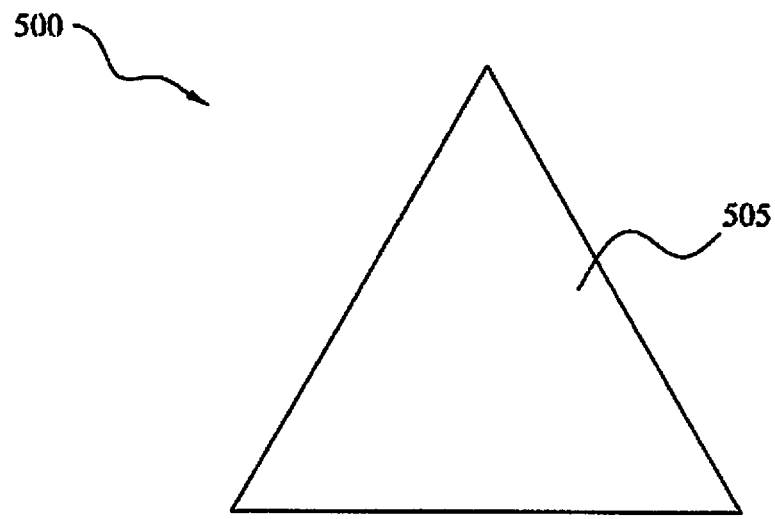
Figure 6:
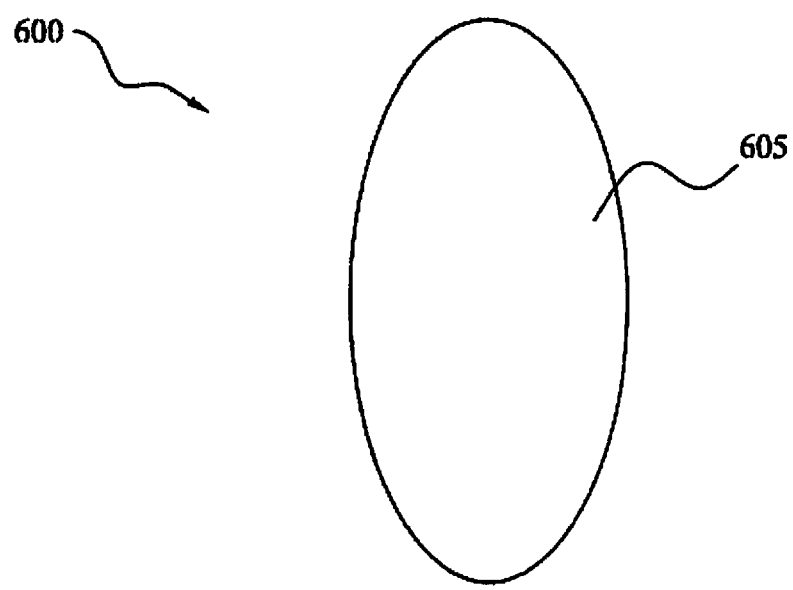

To aid understanding, this document is organized as follows. First, FIGS. 1 and 2 illustrate an exemplary embodiment of the system in which internal antimicrobial and adhesive agents are illustrated. Second, FIG. 3 illustrates an exemplary embodiment of the system in which the malleable or pliable features of the system are shown. Third, FIGS. 4-6 depict exemplary shapes of the system. Then, with reference to FIGS. 7A-7B, a kit for packaging the system is shown. Further detail in reference to FIGS. 4-6 and 7A-7B is available in co-pending U.S. patent application Ser. No. 14/137,757 to Scheremet, et al. and entitled "Kit for Low Profile Thoracic Wound Seal with Laterally-Directed Discharge," of which the entire contents are fully incorporated herein by reference. Then, with reference to FIG. 8, an exemplary application of an exemplary hydrogel wound covering membrane will be described. This will be followed, with reference to FIGS. 9-10, with a detailed description of both a backing layer and a release layer. Then, with reference to FIGS. 11A-12C various geometries of exemplary hydrogel wound covering membranes will be described. Finally, with reference to FIGS. 13-16, implications of folding and rolling exemplary hydrogel wound covering membranes will be disclosed.

FIG. 1 depicts an upper perspective view of an exemplary system 100. The system 100 includes a membrane 105 and a release liner 110. The release liner 110 permits rapid separation when the membrane 105 is needed for use as a wound dressing, for example.

It should be appreciated that the term "membrane" is not meant to be limiting, and may in various implementations comprise a solid, semi-solid, or liquid composition, for example a pad, a patch, or a gel. The membrane 105 may be applied over the wound in one-piece, a patch or a conventional bandage, or the membrane 105 may be spread over the wound, for example, in a liquid or fluid-gel form. The membrane 105 may be formed into shapes of various sizes, for example, 6 inches×6 inches, 12 inches×12 inches, or 4 inches×18 inches.

FIG. 2 depicts a cross-sectional view of the system 100. The membrane 105 includes a carrier substrate 115 comprised of a pliable material, for example, a hydrogel substance. As illustrated, the carrier substrate 115 may be rectangular in shape; however other shapes may be appreciated as will be discussed in reference to FIGS. 4-6.

The carrier substrate 115 includes an impregnated antimicrobial agent 120. The antimicrobial agent 120 may be evenly dispersed throughout the interior and/or exterior of the carrier substrate 115 or may be dispersed throughout only a portion of the carrier substrate 115, for example, along the bottom or contact surface of the carrier substrate 115.

The carrier substrate 115 includes an impregnated adhesive agent 125. The adhesive agent 125 may be evenly dispersed throughout the interior and/or exterior of the carrier substrate 115 or may be dispersed throughout only a portion of the carrier substrate 115, for example, along the bottom or contact surface of the carrier substrate 115. For example, if the adhesive agent 125 is dispersed only along a singular contact surface (e.g., bottom surface) of the carrier substrate 115 of the membrane 105, the non-contact surfaces (e.g., sides, top) of the carrier substrate 115 of the membrane 105 may include a barrier or composition such that would not contain the adhesive agent 125.

In another exemplary embodiment, an adhesive layer (not shown) may be formed or attached along the bottom or contact surface of the carrier substrate 115. Such an adhesive layer may still permit the antimicrobial agent 120 to make contact with the wound or fluids dispersed from the wound. An example of the adhesive layer may include tape, for example, 3M™ MEDIPORE™ TAPE, commercially available from 3M Corp. of Minnesota.

The adhesive agent 125 presents a tacky or sticky property such that the membrane 105 sticks to the supporting structure, for example, the skin of the patient, yet the adhesive agent 125 permits for easy removal of the membrane 105 from the supporting structure without causing a substantial disturbance or pulling on the supporting structure. For example, the disturbance may include the removal of hair, damage to the wound, tearing, or removal of a scab. The adhesive agent 125 also permits for the membrane to be attached to wet or dirty surfaces, thus not requiring the patient to clean the surface around the wound prior to attachment of the membrane 105.

FIG. 3 depicts an exemplary orientation of the system 100, wherein the membrane 105 and attached release liner 110 are in a rolled orientation. Such an orientation of the system 100 may advantageously permit convenient transport and storage of the system, such as in a medical bag or kit. FIG. 3 also illustrates the malleability of the system 100, for example, the membrane 105 being adapted for attachment to various shaped surfaces.

FIGS. 4-6 depict sets of exemplary shapes of the membrane. The embodiments of FIGS. 4-6 may be implemented in a planar (flat) or on a support member with a curved surface (e.g., see membrane support member). It is speculated by the inventors that a curved surface may be advantageous in yielding a reduced tendency for the membrane to become clogged.

More particularly, FIG. 4 illustrates an exemplary embodiment 400 including a membrane 405 having a circular shape. FIG. 5 illustrates an exemplary embodiment 500 including a membrane 505 having a triangular shape. FIG. 6 illustrates an exemplary embodiment 600 including a membrane 605 having an elliptical shape.

Figure 7A:
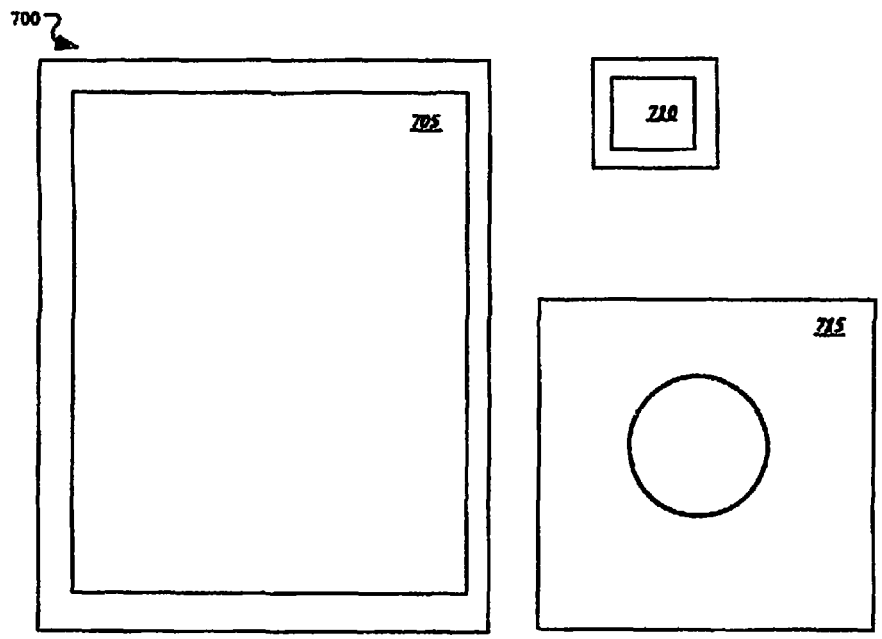
FIGS. 7A-7B depict plan views of exemplary kit for packaging an exemplary membrane.
Figure 7B:
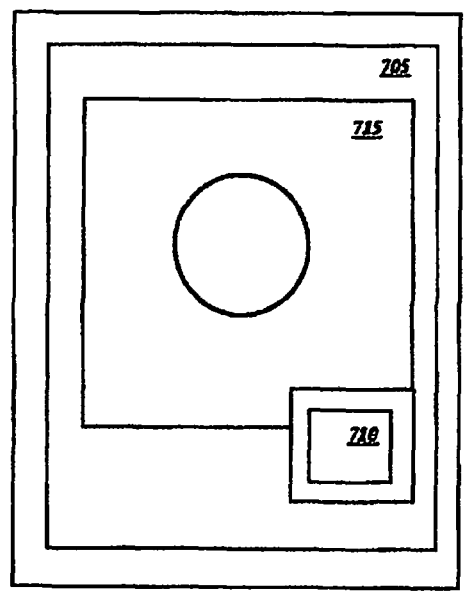

FIGS. 7A-7B depict plan views of an exemplary kit for packaging an exemplary membrane system. It may be advantageous in some applications to have a kit 700 that includes a protective package 705, a pre-moistened antiseptic and/or antimicrobial wipe 710, and a thoracic wound seal 715. In some embodiments, the thoracic wound seal 715 may comprise a release liner to protect the hydrogel adhesive until ready for use. In some implementations, the packaging 705 may serve as a release liner directly, which may reduce the materials and/or manufacturing cost and further reduce the waste stream, for example.

In some implementations, the package 705 may have a foil backing on at least one or both sides. The package 705 may be vacuum sealed to substantially reduce or prevent ingress and/or egress of moisture or contaminants. A vacuum seal may advantageously extend the service life of the hydrogel, for example. In some examples, the kit may include a window on the package 705 to permit inspection of the contents. In some embodiments, the kit 700 may be rolled into a substantially cylindrical form for compact storage (e.g., in a medical bag).

Figure 8:
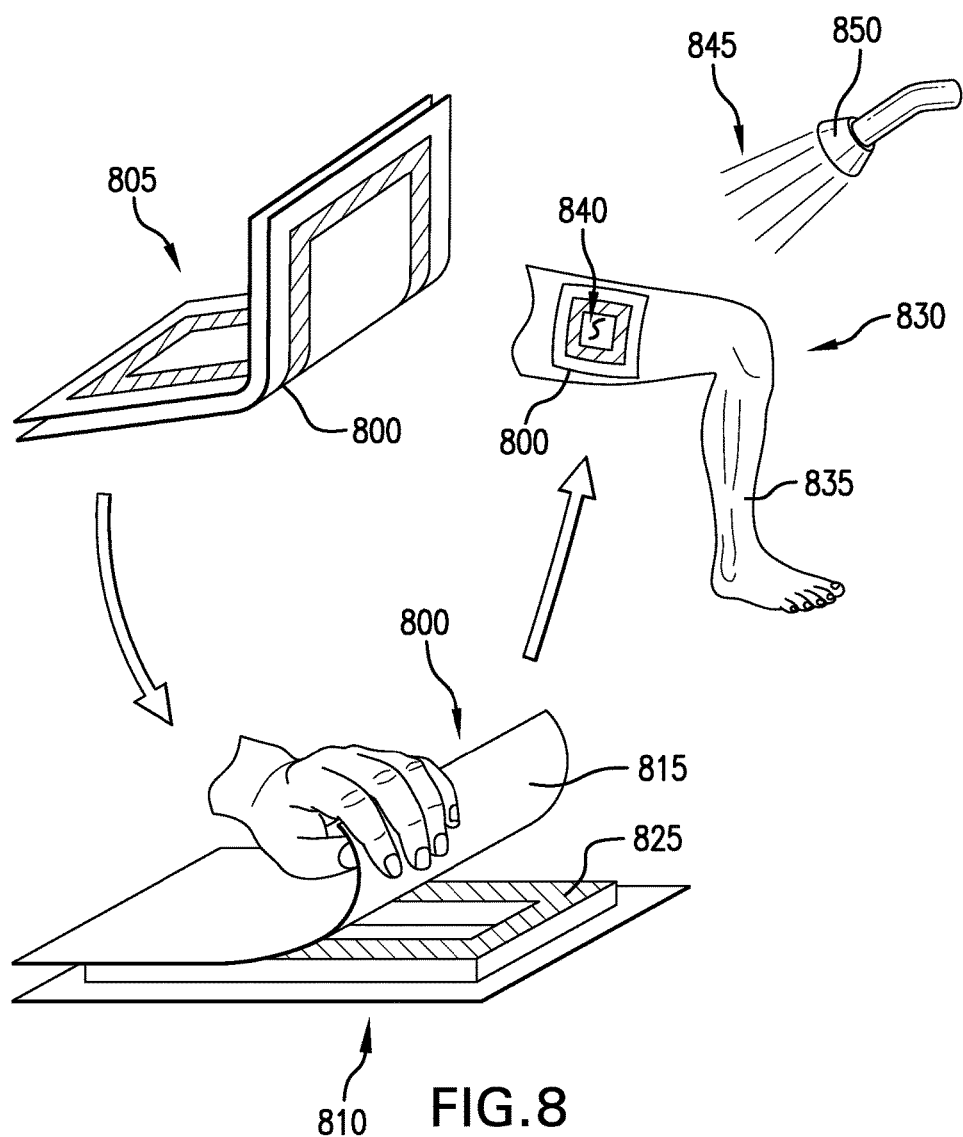
FIG. 8 depicts a triptych of an exemplary hydrogel wound covering membrane unfolded, prepared and applied a leg wound so that a patient can take a shower.

FIG. 8 depicts a triptych of an exemplary hydrogel wound covering membrane unfolded, prepared and applied a leg wound so that a patient can take a shower. In the FIG. 8 triptych, an exemplary wound covering membrane 800 is first unfolded 805. The hydrogel wound covering membrane 800 may have been folded so as to occupy a small space for storage, for example. In the second frame 810 of the triptych, a release liner 815 is being removed from the unfolded hydrogel wound covering membrane 800. The removal of the release liner 815 exposes an adhesion layer 825. The adhesion layer 825 may be part of a hydrogel layer, in some embodiments. In some embodiments, the hydrogel may have an adhesive quality at the exposed surface. In some embodiments, the hydrogel may have an adhesive quality throughout the layer. The third frame 830 of the triptych shows the hydrogel wound covering membrane 800 as it has been applied to a patient's leg 835. The hydrogel wound covering membrane 800 is depicted as transparent so that a wound 840 can be seen on the patient's leg 835. The adhesion layer 825 has circumscribed the wound 840 thereby preventing the wound's exposure to water 845 from a shower head 850. In some embodiments, the hydrogel wound covering membrane may advantageously protect a wound from being contaminated when a patient is exposed to a non-sterile environment.

Figure 9:
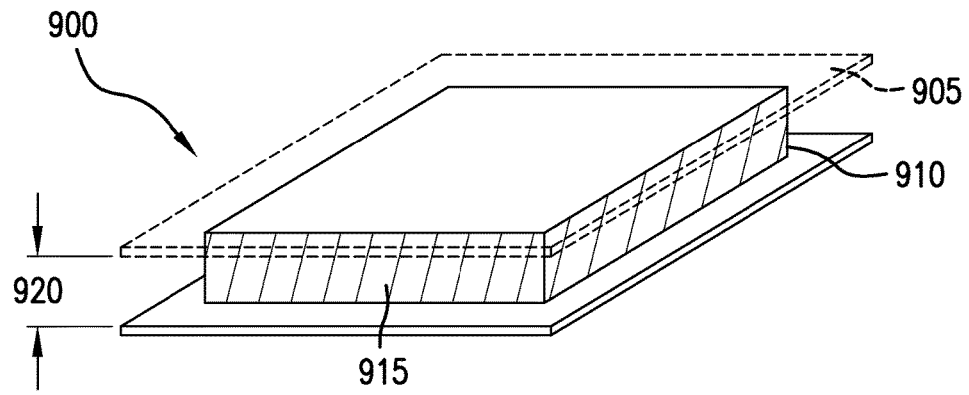
FIG. 9 depicts a perspective view of an exemplary hydrogel wound covering membrane having a backing layer and a release layer.

FIG. 9 depicts a perspective view of an exemplary hydrogel wound covering membrane having a backing layer and a release layer. In the FIG. 9 embodiment, an exemplary hydrogel wound covering membrane 900 includes a backing layer 905 and a release layer 910. A hydrogel layer 915 is shown sandwiched between the backing layer 905 and the release layer 910. The hydrogel layer is shown as having a substantially uniform thickness 920. The hydrogel layer 915 may include antimicrobial agents. In some embodiments, the hydrogel layer 915 may include adhesive agents. Various configurations of antimicrobial and/or adhesive agents may be used in various embodiments. For example, in some embodiments, an adhesive layer may circumscribe an interior which may be substantially non-adhesive hydrogel. In some embodiments, the hydrogel layer may have two sub-layers, one adhesive and a skin adhesive layer, for example. In some embodiments, the hydrogel may have an adhesive homogenously throughout the hydrogel layer. In some embodiments, the microbial agent may be localized to a specific region of the hydrogel layer. In an exemplary embodiment, microbial agents may be homogenously distributed throughout the hydrogel layer, for example.

Figure 10:
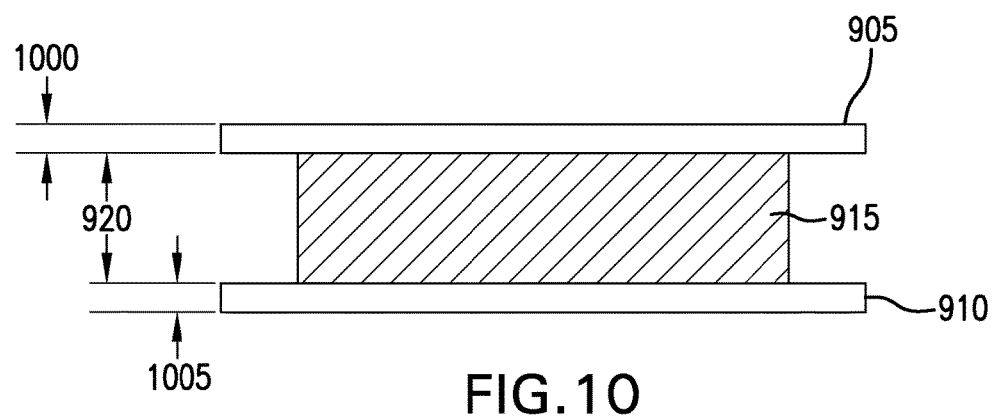
FIG. 10 depicts a side elevation view of an exemplary hydrogel wound covering membrane having a backing layer and a release layer.
Figure 11A:
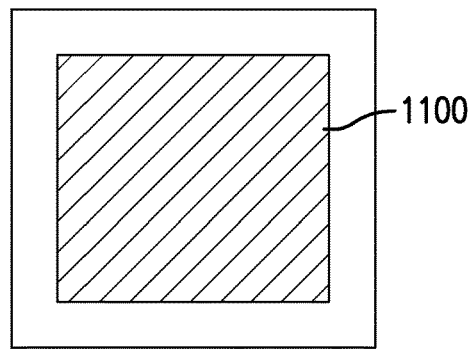
FIGS. 11A-11D depict plan views of various geometries of exemplary hydrogel wound covering membranes.
Figure 11B:
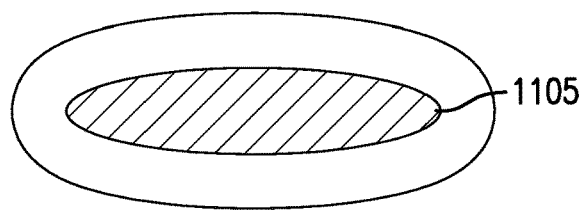
Figure 11C:
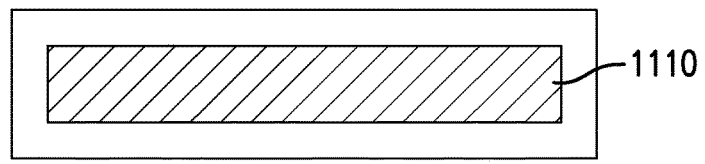
Figure 11D:
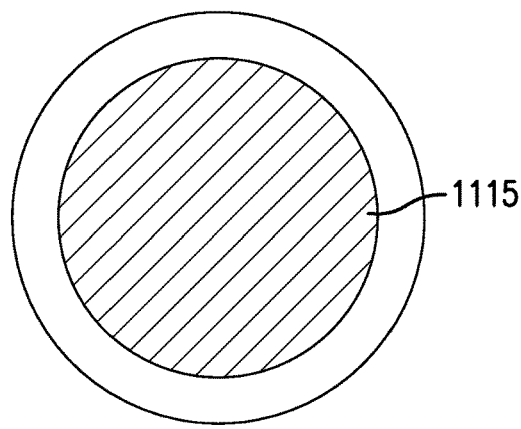

FIG. 10 depicts a side elevation view of an exemplary hydrogel wound covering membrane having a backing layer and a release layer. In the FIG. 10 depiction, the exemplary hydrogel wound covering membrane 900 is depicted from a side elevation view. The hydrogel may have a substantially uniform thickness 920. The backing layer 905 may have a predetermined thickness 1000. The release layer 910 may also have a predetermined thickness 1005. The thicknesses of the backing layer 905 and/or the release layer 910 may be predetermined based upon pliability considerations. For example, the hydrogel wound covering membrane may be nine inches by nine inches square, for example. To better stow such a hydrogel wound covering membrane, folding or rolling of the hydrogel wound covering membrane may be performed. The thicknesses of each of the layers may be selected so that when folded or rolled, the hydrogel layer is not locally thinned, for example, at a folded region. The materials used for the backing layer 905 and/or the release layer 910 may also be predetermined based at least in part upon pliability considerations. For example, a thin layer of Polyvinyl Chloride may be used for either the backing layer or the release layer or both. In some embodiments, a thin film of low-density polyethylene may be used for either the backing layer or the release layer or both. Various other pliant materials may be used for one or both of these layers.

FIGS. 11A-11D depict plan views of various geometries of exemplary hydrogel wound covering membranes. In the FIG. 11A embodiment, a hydrogel wound covering membrane 1100 has a square geometry. In some embodiments, the side length of the square may be various sizes for application to variously sized wounds, for example. In some embodiments a size length may be 4 inches, 6 inches, 7 inches, 9 inches, 12 inches, or any reasonable length for application to a wounded human being. In the FIG. 11B embodiment, an elongated oval shaped hydrogel wound covering membrane 1105 is depicted. In the FIG. 11C embodiment, an elongated rectangular shaped hydrogel wound covering membrane 1110 is depicted. And in the FIG. 11D embodiment, a circular hydrogel wound covering membrane 1115 is depicted. In each of the FIG. 11 depictions, the hydrogel (depicted with diagonal stitching) has no interior voids, but is contiguous throughout each of the membrane geometries. In such embodiments, as depicted in FIGS. 11A-11D, the hydrogel may contacts the wound, if a gauze or other barrier is not interposed between the hydrogel and the wound. In some embodiments, a gauze may be affixed to a center portion of the hydrogel wound covering membrane. In some embodiments, the gauze may be affixed to the hydrogel in a center portion of the membrane. In some embodiments, the gauze may replace the hydrogel in a center region of the membrane, for example.

Figure 12A:
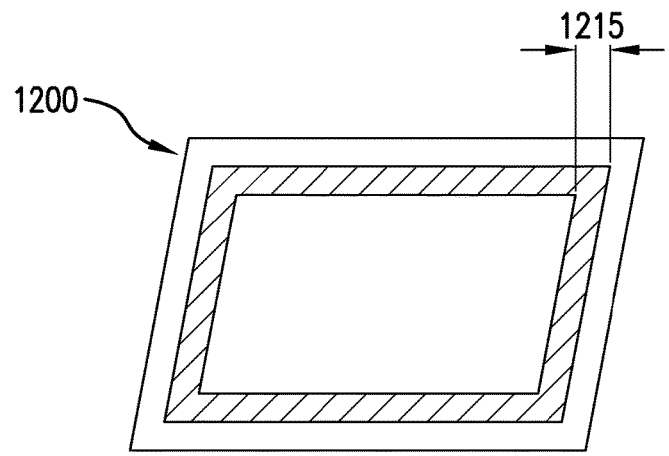
FIGS. 12A-12C depict plan views of various geometries of exemplary hydrogel wound covering membranes having only peripheral adhesion.
Figure 12B:
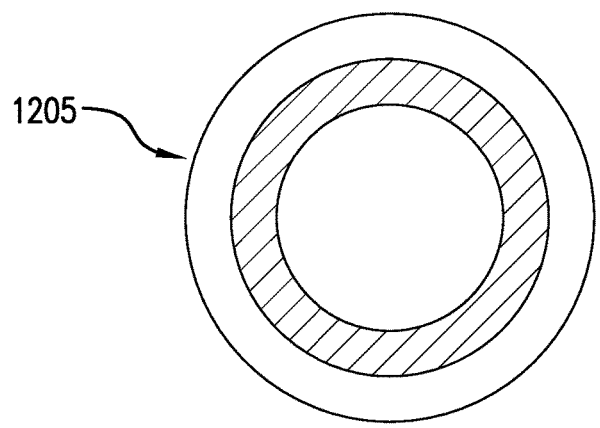
Figure 12C:
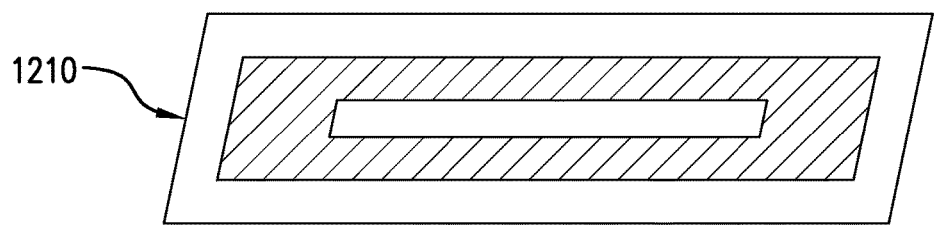

FIGS. 12A-12C depict plan views of various geometries of exemplary hydrogel wound covering membranes having only peripheral adhesion. In the FIGS. 12A-12C embodiments, exemplary hydrogel wound covering membranes that have no hydrogel in a central region are depicted. In the FIG. 12A embodiment, an exemplary rectangular hydrogel wound covering membrane 1200 having hydrogel only around a periphery is depicted. In the FIG. 12B embodiment, an exemplary circular hydrogel wound covering membrane 1205 having an annular hydrogel region is depicted. In the FIG. 12C embodiment, an elongate rectangular hydrogel wound covering membrane 1210 having a narrow central portion that has no hydrogel is depicted Annular type hydrogel wound covering membranes may advantageously be quickly affixed to a wearer without exposing the wound to hydrogel. The affixed hydrogel wound covering membrane may be worn temporarily, for example, during baths and/or showers. The thickness of the annulus 1215 may be predetermined based upon the considerations of how long the seal must remain secure. For example, if a hydrogel wound covering membrane is intended to remain in water for an hour, the annular seal must be thick enough to prevent the hydrogel wound covering membrane from releasing from the patient's skin.

Figure 13:
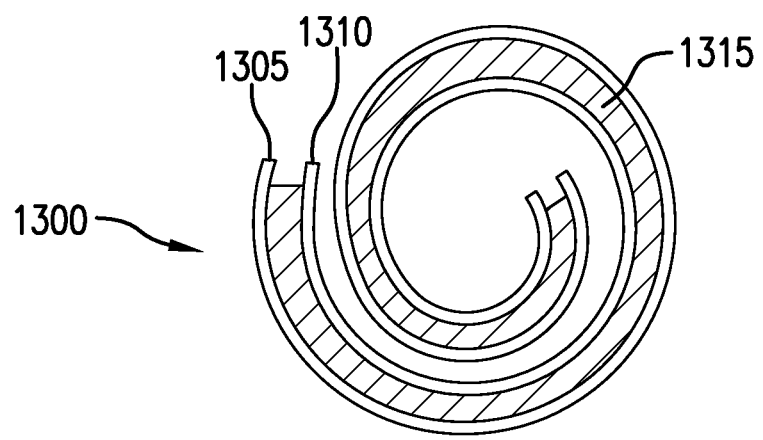
FIG. 13 depicts a cross-sectional view of an exemplary hydrogel wound covering membrane rolled for stowage.

FIG. 13 depicts a cross-sectional view of an exemplary hydrogel wound covering membrane rolled for stowage. In the FIG. 13 embodiment, an exemplary hydrogel wound covering membrane 1300 is depicted in a rolled configuration. Such a configuration may be used, for example, to provide a compact volume for stowage. When rolling the hydrogel wound covering membrane 1300, a backing layer 1305 and a release liner 1310 may be rolled in a spiral fashion as depicted. The backing layer 1305 and the release liner 1310 may sandwich a hydrogel layer 1315. The relative thicknesses of these three layers may be selected based upon maintaining a substantially uniform hydrogel layer 1315 thickness, for example. The pliability of the backing layer 1305 and/or the release liner 1310 may be selected to be small with respect to the hydrogel layer's resistance to deformation, for example. The ratio of the pliability of the backing layer and/or the release liner to the hydrogel layer's resistance to deformation may be selected to be less than a predetermined threshold, for example.

Figure 14:
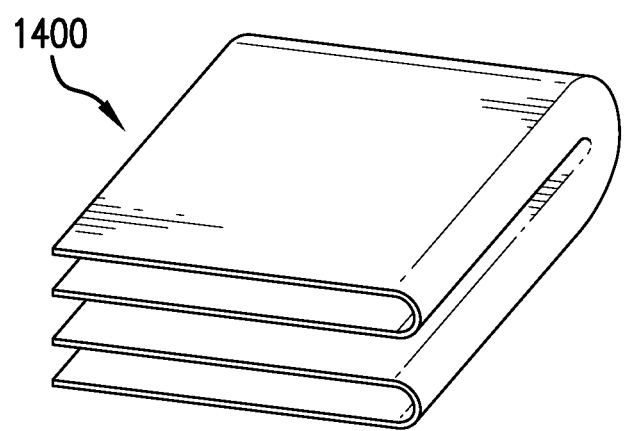
FIG. 14 depicts a perspective view of an exemplary hydrogel wound covering membrane folded for stowage.
Figure 15:
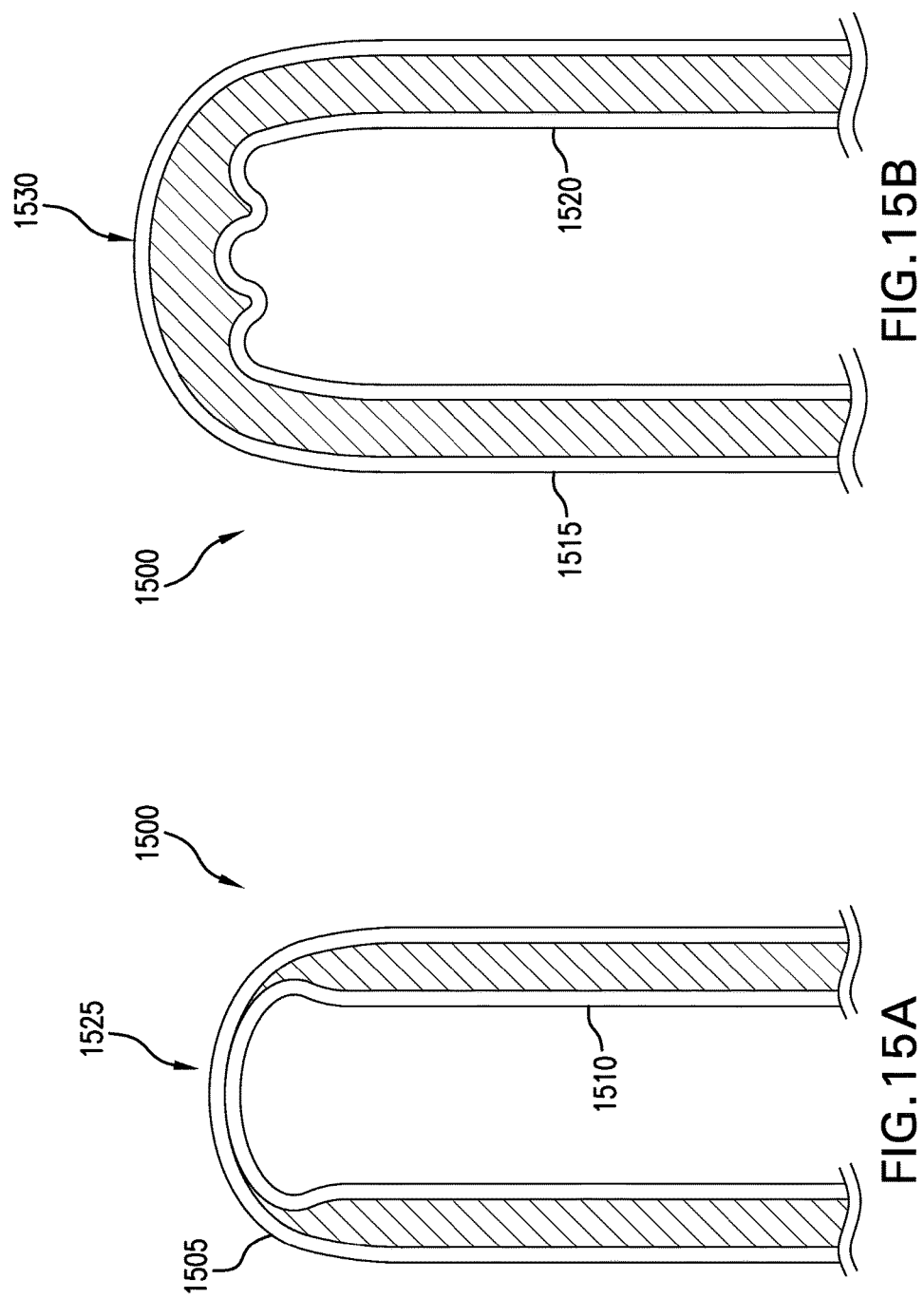
FIGS. 15A-15B depict cross-sectional views of exemplary folded hydrogel wound covering membranes.

FIG. 14 depicts a perspective view of an exemplary hydrogel wound covering membrane folded for stowage. In the FIG. 14 depiction, an exemplary hydrogel wound covering membrane 1400 has been folded in two directions. The hydrogel wound covering membrane 1400 may be folded in such a way so as to occupy a predetermined storage volume, for example. In some embodiments, the hydrogel wound covering membrane may be an element of a first aid kit, for example. The hydrogel wound covering member may occupy a specific storage location in the kit's carrying case, for example. The folded regions of the hydrogel wound covering membrane may retain a substantially equal thickness as the unfolded regions, in some embodiments.

FIGS. 15A-15B depict cross-sectional views of exemplary folded hydrogel wound covering membranes. In the FIG. 15A depiction, a close-up of the folded region of an exemplary hydrogel wound covering membrane 1500 is depicted. The hydrogel wound covering membrane has a backing layer 1505 and a release liner 1510. In the FIG. 15A embodiment, the pliabilities of both the backing layer 1505 and the release liner 1510 are less than the pliabilites of both the backing layer 1515 and the release liner 1520 of the FIG. 15B embodiment. The FIG. 15A embodiment has pinched the hydrogel in the folded region 1525. But in the folded region 1530 of the FIG. 15B embodiment, the hydrogel has a folded region thickness that is substantially equal to the thickness of the unfolded region. The backing layer 1515 and the release liner 1520 are depicted as being thinner in the FIG. 15B embodiment, than the backing layer 1505 and the release line 1510 in the FIG. 15A embodiment. The thickness difference represents an increase pliability of the FIG. 15B embodiment's layers than the corresponding layers of the FIG. 15A embodiment. The pliability may be increased, however, by choice of materials in some examples, instead of or in addition to choice of thickness, for example.

Figure 16:
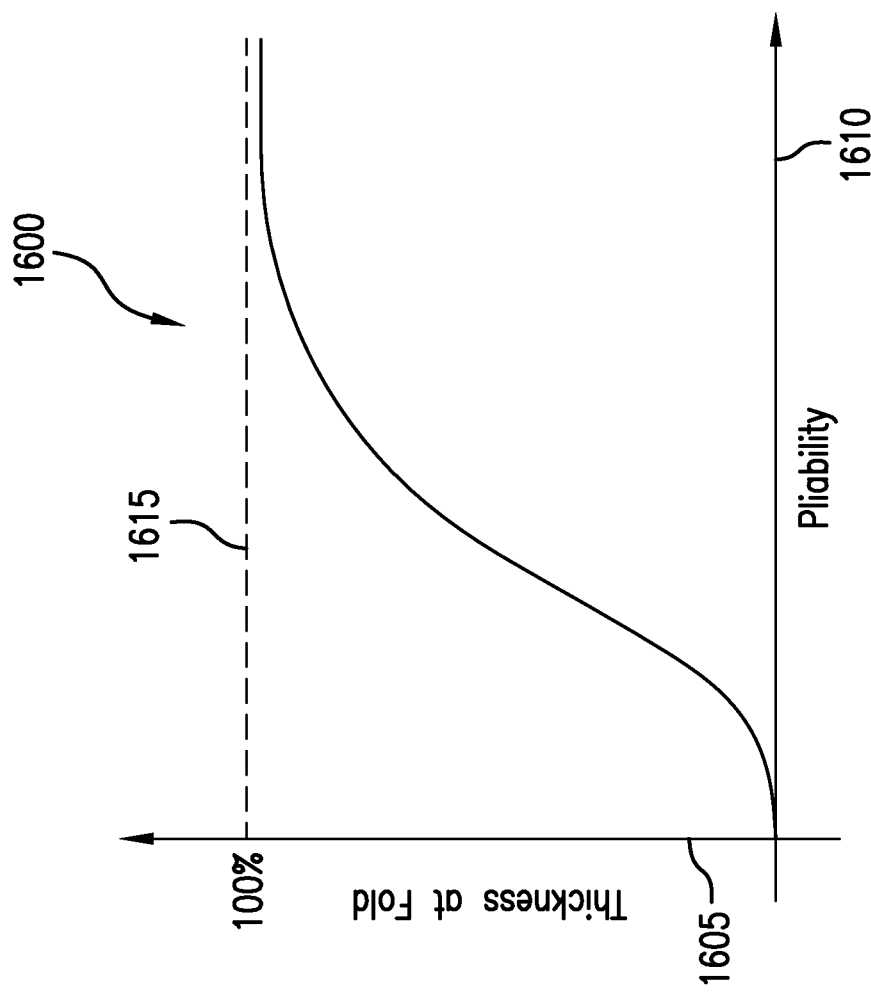
FIG. 16 depicts a graph showing an exemplary relation between the pliability of a backing layer and the thinning of the hydrogel at a fold location.

FIG. 16 depicts a graph showing an exemplary relation between the pliability of a backing layer and the thinning of the hydrogel at a fold location. In the FIG. 16 graph 1600, a thickness of the hydrogel layer at a folded region is plotted on a vertical axis 1605 versus a pliability of a release liner and/or a backing layer on a horizontal axis 1610. The relation 1615 shows that as the pliability of the layer increases, the thickness of the hydrogel layer at the folded region increases. And as the pliability of the layer decreases, the thickness of the hydrogel layer may decrease to zero as it becomes pinched off. For highly pliant layers, the thickness of the hydrogel layer may asymptotically approach the thickness 1615 of the hydrogel at non-folded locations.

In an exemplary embodiment, a hydrogel wound covering membrane may have a thoracic valve. The thoracic valve may provide for unidirectional fluid flow. The hydrogel wound-covering membrane may circumscribe the thoracic valve. When attached to a skin surface of a human body, a hydrogel seal may circumscribe the thoracic valve. Exemplary thoracic valves are disclosed in related copending application U.S. Ser. No. 13/647,369 titled "Kit for Low Profile Thoracic Wound Seal with Laterally-Directed Discharge," filed Oct. 8, 2012, the entire disclose of which is herein incorporated by reference. For example, exemplary thoracic valves are described throughout the specification, including, for example, at [0023-0045] and FIGS. 1A-3B.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are contemplated.

What is claimed is:

1. A wound covering dressing for forming a peripheral seal to skin around a wound, the dressing comprising:
    a dressing having a predetermined size and a predetermined shape to define a central region of the dressing for covering a wound of the skin of a patient, and to further define a sealing region that completely encompasses the central region of the dressing;
    an adhesive hydrogel disposed in the sealing region of the dressing to form a seal between the dressing and a region of the skin that encompasses the wound; and,
    a release liner disposed on a wound facing surface of the adhesive hydrogel,
    wherein the central region of the dressing is devoid of the adhesive hydrogel, and outer edge of the sealing region of the dressing has a shape corresponding to the predetermined shape of the dressing, an outer edge of the sealing region lies within a peripheral outline of an outer edge of the dressing, and, when the sealing region is sealed to the skin around the wound, the sealing region peripherally encompassed the wound such that the wound is entirely sealed and encompassed by the surrounding skin, the adhesive hydrogel, and the dressing,
    wherein the wound covering dressing and the release liner are both foldable,
    wherein the adhesive hydrogel has a substantially uniform thickness between the dressing and the release liner,
    wherein the release liner has a pliability effective to prevent pinching of the adhesive hydrogel when the wound covering dressing and the release liner are both folded.

2. The wound covering dressing of claim 1, wherein the thickness of the adhesive hydrogel is predetermined based upon the desired length of time for the wound covering dressing to encompass the wound.

3. The wound covering dressing of claim 1, further comprising an antimicrobial agent disposed on a wound facing surface of the adhesive hydrogel.

4. The wound covering dressing of claim 1, further comprising a backing layer disposed between the dressing and the adhesive hydrogel, the backing layer having a predetermined thickness based on a desired level of pliability.

5. The wound covering dressing of claim 1, wherein the dressing comprises a substantially elliptical shape.

6. The wound covering dressing of claim 1, wherein the dressing comprises a substantially rectangular shape.

7. The wound covering dressing of claim 1, wherein the dressing comprises a substantially triangular shape.

8. The wound covering dressing of claim 1, wherein the dressing comprises a substantially circular shape.

9. A wound covering dressing for forming a peripheral seal to skin around a wound, the dressing comprising:
    a dressing having a predetermined size and a predetermined shape to define a central region of the dressing for covering a wound of the skin of a patient, and to further define a sealing region that completely encompasses the central region of the dressing; and,
    an adhesive hydrogel disposed in the sealing region of the dressing to form a seal between the dressing and a region of the skin that encompasses the wound; and,
    a release liner disposed on a wound facing surface of the adhesive hydrogel having a predetermined thickness based on a desired level of pliability,
    wherein the central region of the dressing is devoid of the adhesive hydrogel, an outer edge of the sealing region of the dressing has a shape corresponding to the predetermined shape of the dressing, an outer edge of the sealing region lies within a peripheral outline of an outer edge of the dressing, and, when the sealing region is sealed to the skin around the wound, the sealing region peripherally encompasses the wound such that the wound is entirely sealed and encompassed by the surrounding skin, the adhesive hydrogel, and the dressing, and, wherein the adhesive hydrogel includes an antimicrobial agent adapted to release towards the wound facing surface of the hydrogel when the release liner is removed from the adhesive hydrogel, wherein the wound covering dressing and the release liner are both foldable, wherein the adhesive hydrogel has a substantially uniform thickness between the dressing and the release liner, wherein the release liner has a pliability effective to prevent pinching of the adhesive hydrogel when the wound covering dressing and the release liner are both folded.

* * * * *